(12) United States Patent
Geiselhart

(10) Patent No.: US 8,951,246 B2
(45) Date of Patent: Feb. 10, 2015

(54) CRYOSURGICAL DEVICE WITH A PROBE COUPLING FORMED FROM THE SOCKET AND THE PLUG OF CRYOPROBES

(75) Inventor: Franz Geiselhart, Reutlingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1712 days.

(21) Appl. No.: 12/097,491

(22) PCT Filed: Nov. 22, 2006

(86) PCT No.: PCT/EP2006/011199
§ 371 (c)(1),
(2), (4) Date: Jun. 13, 2008

(87) PCT Pub. No.: WO2007/073810
PCT Pub. Date: Jul. 5, 2007

(65) Prior Publication Data
US 2008/0319433 A1    Dec. 25, 2008

(30) Foreign Application Priority Data

Dec. 16, 2005 (DE) .......... 10 2005 060 389
Jan. 25, 2006 (DE) .......... 10 2006 003 571

(51) Int. Cl.
*A61B 18/02* (2006.01)
*A61B 17/00* (2006.01)

(52) U.S. Cl.
CPC .......... *A61B 18/02* (2013.01); *A61B 2018/0231* (2013.01); *A61B 2017/00477* (2013.01); *A61B 2018/0212* (2013.01); *A61B 2018/0262* (2013.01)
USPC .................. 606/20; 606/21; 606/22

(58) Field of Classification Search
CPC .............. A61B 18/00011; A61B 2018/00017; A61B 2018/00023; A61B 2018/00029; A61B 2018/00035
USPC ...................................... 606/20–26
See application file for complete search history.

(56) References Cited

U.S. PATENT DOCUMENTS

| | | | |
|---|---|---|---|
| 3,536,075 A * | 10/1970 | Thomas, Jr. ............. | 606/23 |
| 3,933,156 A * | 1/1976 | Riggi .................... | 606/25 |
| 4,146,030 A | 3/1979 | Holroyd | |
| 5,520,682 A * | 5/1996 | Baust et al. ............. | 606/24 |
| 5,674,218 A * | 10/1997 | Rubinsky et al. ........ | 606/20 |
| 5,992,158 A * | 11/1999 | Goddard et al. ......... | 62/51.2 |
| 2004/0078033 A1* | 4/2004 | Levin ................... | 606/20 |
| 2008/0119834 A1* | 5/2008 | Vancelette et al. ....... | 606/20 |

FOREIGN PATENT DOCUMENTS

| | | |
|---|---|---|
| DE | 29 812 500 | 10/1998 |
| GB | 2 093 964 | 9/1982 |
| GB | 2 289 413 | 11/1995 |

OTHER PUBLICATIONS

English Translation of Written Opinion of the International Searching Authority, Jul. 8, 2008.

* cited by examiner

*Primary Examiner* — Jaymi Della
(74) *Attorney, Agent, or Firm* — Dickstein Shapiro LLP

(57) ABSTRACT

A cryosurgical device, with a control for the supply and/or removal of a coolant gas to a cryoprobe via a return flow or a supply flow. The device has at least one socket for the attachment of a rigid cryoprobe and a flexible cryoprobe. The socket and the plugs of the cryoprobes each form probe couplings. The configuration of the cryosurgical device allows both rigid and flexible cryoprobes to be automatically connected to the appropriate return flow conduit, independently of the level of knowledge of operating personnel.

12 Claims, 6 Drawing Sheets

CRYOSURGICAL DEVICE WITH A PROBE COUPLING FORMED FROM THE SOCKET AND THE PLUG OF CRYOPROBES

FIELD OF THE INVENTION

The invention relates to a cryosurgical device with a probe coupling formed from a socket and a plug of cryoprobes and, more specifically, to a cryosurgical device with a control for the supply and/or removal of coolant gas.

BACKGROUND OF THE INVENTION

Cryosurgical devices are used in surgery wherever they are of a particular advantage or where high-frequency surgery or other methods cannot be used. For example, due to their unfavourable distribution, it is not really feasible to cut tumors out of the liver. Instead, in such cases, pathologically degenerated tissue is killed by means of deep freezing and then left in the body. Also, with the availability of flexible probes, foreign bodies may be extracted from body cavities by freezing them solid onto the cryoprobe. For example, peanut kernels which have been swallowed and then inadvertently inhaled must be removed from the respiratory tract. It is not possible to use mechanical gripping methods because the risk of crumbling the peanut kernels is too high.

There are various methods which may be used for deep-freezing during surgery. One of these is based on the Joule-Thomson effect, wherein the atoms or molecules of a gas expanding below the inversion temperature work against the mutual attraction so that the gas loses internal energy, and therefore cools down. This effect is used with a variety of cryosurgical methods. The expanding gas—hereinafter called working gas—is usually $CO_2$ or $N_2O$ (which is also known as laughing gas in anaesthesia) because these gases are widely used in medicine for various reasons. They are neither flammable nor toxic, they have a high Joule-Thomson coefficient ($\mu$) and they are liquefiable at normal temperature, allowing a gaseous phase to be held under constant pressure above the liquid phase in the pressure cylinder.

Cryosurgical devices of the above-described kind have a reservoir, which holds a sufficient amount of working gas, probes, which are applied on the area in the body to be treated, and conduits, which pass through the probes and discharge the working gas into the inner lumen of the probes where it expands and, as a result, cools the tips of the probes. The probes are preferably made of a thermally conductive material, thereby ensuring the dissipation of the tissue heat via the probes and hence, a cooling effect.

When the tissue or possible foreign body that is to be deep-frozen has cooled to a sufficiently low temperature, thawing should start at a specified time. However, it is desired that this should not require any further devices on the device to make the thawing possible. It is advantageous to simply reverse the Joule-Thomson effect, meaning the gas is compressed below the inversion temperature. For this, the probes have to be connected to a deaerator which in turn has a valve. The probe must be able to withstand a pressure that occurs in the event of valve failure if the probe continues to be filled with gas. For this, the probe must have a pressure-resistant design. Therefore, only rigid probes can be considered for this valve design. To ensure safety in non-rigid (e.g., flexible) probes, the gas passage is preferably provisionally diverted with external hoses around the return flow valve and in this way the working gas supplied to the gas disposal. Malfunctions of the device can occur if the external connection for this procedure is not fully closed. If, in this regard, the working gas is simply discharged into the ambient air of the operating theatre. If this occurs, it is easily possible, in particular in the case of laughing gas, for the maximum allowable workplace concentration (MAC) of 100 ppm to be exceeded.

It is an object of the present invention to develop a cryosurgical device of the above described type that does not have the described drawbacks and can be safely operated regardless of the level of knowledge of the operating personnel.

SUMMARY

In particular, the object of the present invention may be achieved by a cryosurgical device with a control for the supply and/or removal of a coolant gas to a cryoprobe via a return flow or a supply flow and with at least one socket for the attachment of at least a first cryoprobe and a second cryoprobe, which requires a different backflow pressure in its return flow conduit than the first cryoprobe, wherein the plugs on the cryoprobes and the socket form a probe coupling in which the socket comprises at least two return flow conduits and/or supply flow conduits and the first cryoprobe has a plug which differs from the plug of the second cryoprobe in that the removal and/or supply of the coolant gas from/to the second cryoprobe on insertion into the socket takes place via different return flow conduits and/or supply flow conduits than the removal or supply of the coolant gas from/to the first cryoprobe on insertion into this socket.

By using the invention, different cryoprobes, be they rigid or flexible, can be simply and reliably connected to the same cryosurgical device, independent of the level of knowledge of the operating personnel, while ensuring safety of operation. In this regard, the coupling geometry itself ensures the correct return flow for rigid cryoprobes (via a conduit with a valve) and for flexible cryoprobes (via a conduit without a valve) in the gas disposal device.

In a first embodiment of the invention, the supply flow conduits and return flow conduits belonging to the probe coupling are connected by the socket directly to a gas disposal device of the cryosurgical device. This means that, when using flexible probes, the operating personnel no longer have to provisionally divert the return flow for the gas disposal of the cryosurgical device externally around the return flow valve with hoses which are generally not intended for this purpose and hence the possible malfunctions due to the "non-closure" of the connection and the possible exceeding of workplace concentrations of the coolant gas are avoided.

In addition, the insertable plug-in regions of the cryoprobe plug have a round cross section and grooves surrounding the plug-in region at each of the openings of the supply flow conduit and return flow conduit. The grooves do not have to be made separately for this. The distance between the seals results in the formation of annular chambers which are suitable to serve as gas channels. This enables the plugs to be plugged into the socket in a simple way by the operating personnel, wherein the supply flow and the return flow of the coolant gas to the corresponding cryoprobes is ensured in any possible position of the inserted plug-in region and the possibility of errors due to faulty insertion is avoided.

In addition, the grooves of the return flow conduit and of the supply flow conduit of the respective plug-in region and of a corresponding socket region of the socket are separated from each other in a gas-tight way by seals, in particular by O-rings in order to ensure the corresponding connection between the return flows and supply flows between the socket and plug-in region, wherein the supply flow conduit of the first cryoprobe and the second cryoprobe is arranged at the same position on the plug and on the socket so that for the rigid and flexible probe, the supply flow of the coolant gas through the supply flow conduit from the reservoir of the cryosurgical device via the socket region into the supply flow of the corresponding plug-in region is ensured. In addition, the return flow conduit of a first rigid cryoprobe via a conduit with a valve and the return flow conduit of a second flexible cryoprobe via a conduit without a valve lead to the gas disposal device of the cryosurgical device. This means that the rigid cryoprobe can be heated using the reverse Joule-Thomson effect, wherein the gas is compressed below the inversion temperature by the valve disposed in the conduit and the coolant gas in the flexible probe can be led off without compression through a valve, and hence without the risk of an accident due to an unforeseen pressure build-up, into the gas disposal device of the cryosurgical device.

It is also possible for the plug-in region in the socket of the cryosurgical device to have a fixable design. This ensures that the plug is not pushed out of the socket by any possible pressure from the supply and return flow of coolant gas or that the coolant gas in the supply flow and/or return flow does not enter a non-intended supply flow and/or return flow. Hereby, the seal can be implemented, for example, by an external thread on the socket and a correspondingly attached nut at the plug-in region, by a detachable click seal, by a detent corresponding to a detachable seal, or by a magnet attached at the lower end of the plug-in region and/or metal plate or magnet attached in the lower socket region. A deaeration opening in the rear part of the socket makes plugging in easier because the insertion is unable to form an air cushion. Furthermore, this ensures that no axial forces from pressure push the plug out again. In this case, there is no need to fix the plug.

In another embodiment of the invention, the plug-in region of the first and second cryoprobe can be formed by a separate adapter, wherein the first and second plug-in regions are adapted to a first or second conventional cryoprobe. This ensures that older models of various cryoprobes can also be used with the cryosurgical device of the present invention. In addition, the socket region can also be formed by a separate adapter, wherein the separate adapter is connected via conduits to the control of the cryosurgical device and/or the reservoir for coolant gas and/or the valve and/or the gas disposal device for the return flow of coolant gas. This means that older models of the cryosurgical device can also be used for the insertion of the cryoprobes of the present invention and/or for the insertion of older cryoprobes with corresponding adapters.

A further embodiment of the invention provides that the probe coupling is contained in a cryosurgical device with a device for controlling ice-ball formation, wherein the ice-ball formation is controlled by an electromagnetic field surrounding the ice ball. This enables rigid and flexible probes with electrical regions for the generation of the electromagnetic field to be simply and reliably plugged into the corresponding cryosurgical device.

BRIEF DESCRIPTION OF THE DRAWINGS

In the following, the invention will now be described in more detail with reference to an exemplary embodiment, which will be explained in more detail with reference to the enclosed drawings.

DETAILED DESCRIPTION OF THE INVENTION

In the following description, the same reference numbers are used for identical parts and parts with an identical function.

Figure 1:
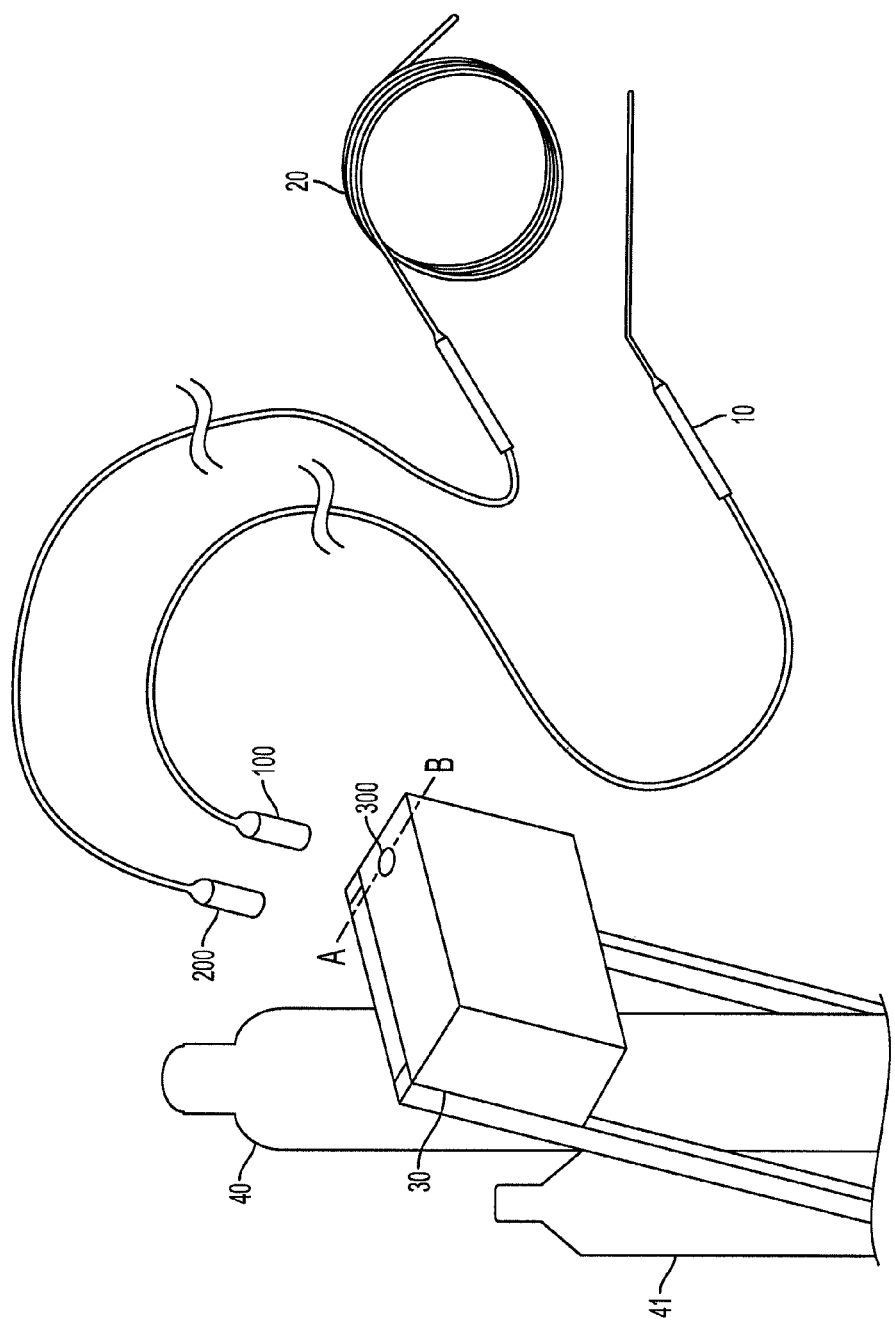
FIG. 1 illustrates a perspective view of a cryosurgical device with a rigid probe and a flexible probe.

The exemplary embodiment in FIG. 1 shows a cryosurgical device with a control 30, a reservoir 40, a container for the gas disposal 41, a rigid first probe 10 and a flexible second probe 20. The control 30 of the cryosurgical device comprises a socket 300 for the attachment of the rigid first probe 10 or for the attachment of the flexible second probe 20, wherein a plug 100 of the rigid first cryoprobe 10 or a plug 200 of the flexible second cryoprobe 20 and the socket 300 of the cryosurgical device form a probe coupling. The reservoir 40 of the cryosurgical device is filled with a coolant gas for cooling the corresponding cryoprobe 10, 20 and is connected via conduits to the control 30 and a supply flow conduit 304 (see FIG. 2b) of the socket 300. The gas disposal device 41 is connected to a respective return flow conduit 102b, 202b (see FIG. 2b, 3b) of the cryoprobes 10, 20 via both return flow conduits 302, 303 of the socket 300, once with a valve 305 and once without a valve.

Figure 2A:
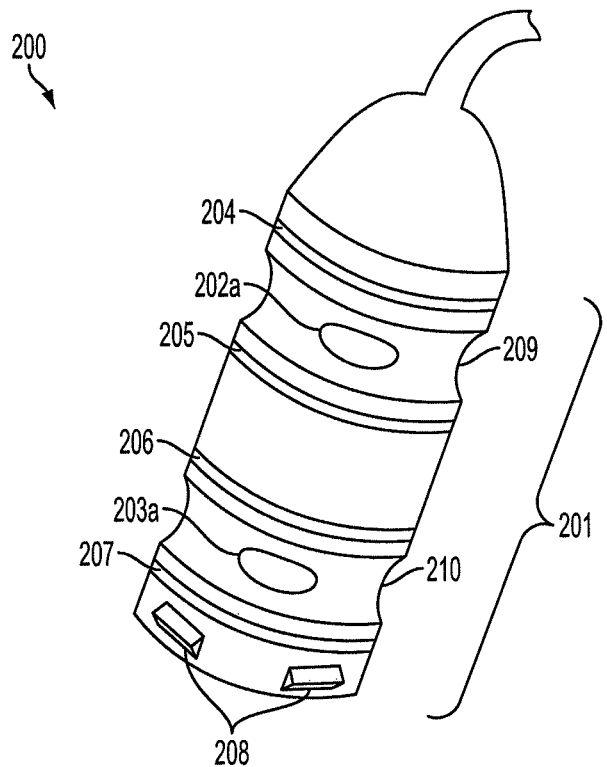
FIG. 2a illustrates a perspective view of a plug-in region of a rigid cryoprobe.

FIG. 2a shows a perspective view of the plug 200 of the flexible second cryoprobe 20. A plug-in region 201 has two circular openings 202a, 203a, wherein the opening 202a is arranged at the upper end of the plug-in region 201 and the opening 203a is arranged at the lower end of the plug-in region 201. At the respective height of the openings 202a, 203a, there is a groove 209, 210 surrounding the plug-in region 201 with a width at least that of the respective opening 202a, 203a. Arranged on both sides of the respective openings 202a, 203a and grooves 209, 210 are circumferential seals 204, 205, 206, 207 corresponding to the plug-in region 201 in such a way that, in the inserted condition of the plug 200, they ensure a gas-tight separation between the supply flow conduit 304, 203b and the return flow conduit 302, 202b. In the plug 200 shown in FIG. 2a, at the lower end of the plug-in region 201, there is a fixing 208 which is detachable by a detent and which on insertion snaps into the notches 306 arranged correspondingly in the socket region 201.

The structure of the present probe coupling and the action between the plug 200 and the socket 300 of the cryosurgical device will be explained in more detail with reference to the sectional drawing of the plug-in region 201 inserted in a socket region 301 shown in FIG. 2b.

Figure 2B:
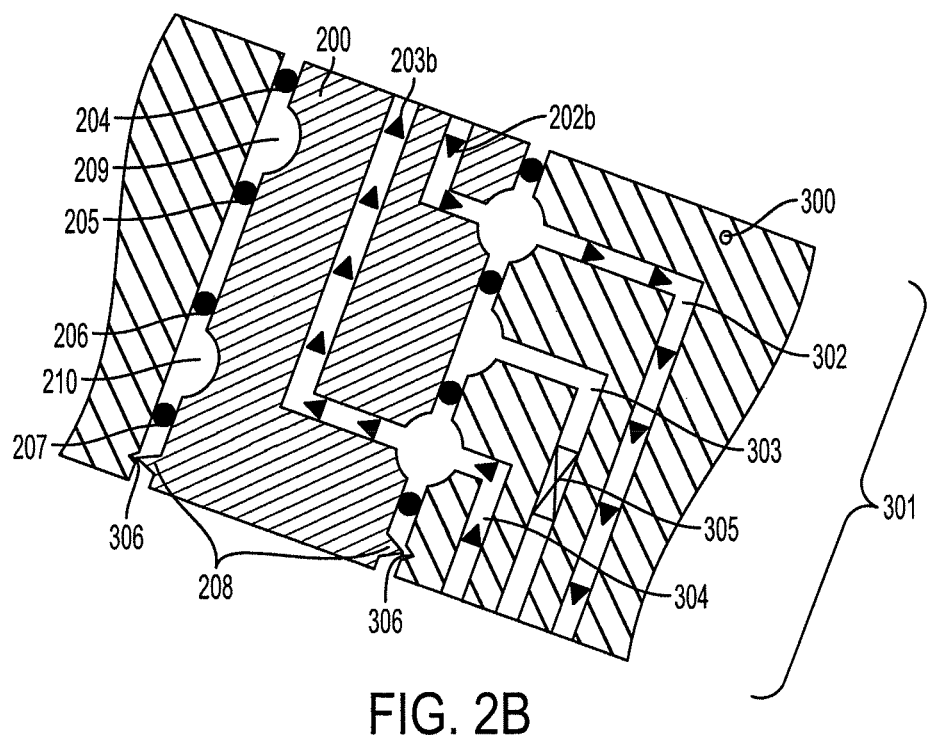
FIG. 2b illustrates a sectional view along the line A-B in FIG. 1 of a plug-in region plugged into a socket.

In the control 30 of the cryosurgical device, the supply flow conduit 304 and the two return flow conduits 302, 303 lead to the socket region 301 of the socket 300, wherein in the exemplary embodiment in FIG. 2b, the return flow conduit 302 of the socket 300 (e.g., the conduit without valve 305) is connected to the return flow conduit 202b of the flexible second cryoprobe 20 and the supply flow conduit 304 is connected to the supply flow conduit 203b of the flexible second cryoprobe 20. This ensures that the coolant gas is diverted by valve 305 from the flexible second cryoprobe 20 into the gas disposal device 41 without any corresponding pressure build-up and hence any potential damage to the flexible second cryoprobe 20 is avoided. When the plug 200 of the flexible second cryoprobe 20 is inserted in the socket 300 of the cryosurgical device, the fixing 208 latches into the corresponding notches 306 of the socket 300 and hence ensures that the plug 200 is held reliably in the socket 300. By the insertion of the plug 200, the supply flow conduit 304 of the control 30 is automatically connected to the supply flow conduit 203b of the flexible second cryoprobe 20. In addition, the return flow conduit 302 of the control 30 leading to the gas disposal device 41 is connected to the return flow conduit 202b of the flexible second cryoprobe 20, wherein the return flow conduit 302 of the control 30 leads past the valve 305 and hence directly into the gas disposal device 41. The grooves 209, 210 surrounding the openings 202, 203 ensure that the supply and return flow of the coolant gas is ensured in every possible position of the inserted plug 200.

Figure 3A:
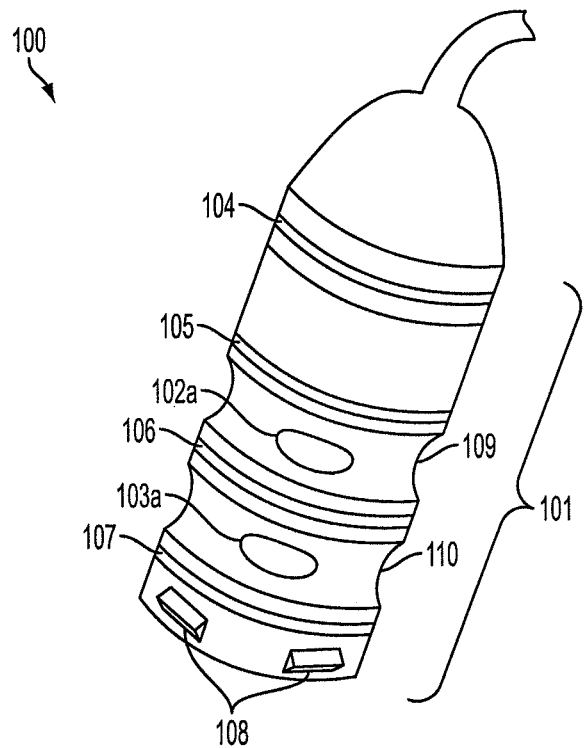
FIG. 3a illustrates a perspective view of a plug-in region of a flexible cryoprobe.

FIG. 3a is a perspective view of a plug 100 of a rigid first cryoprobe 10. A plug-in region 101 has two circular openings 102a, 103a, wherein the opening 102a in the middle region of the plug-in region 101 is arranged between seals 105 and 106 and an opening 103a at the lower end of the plug-in region 101 is arranged between the seals 106 and 107. At the respective height of openings 102a, 103a, there is a groove 109, 110 surrounding the plug-in region 101 with a width at least that of the respective opening 102a, 103a. The seals 104, 105, 106 and 107 are arranged so that in the inserted condition of the plug 100, they ensure a gas-tight separation between the supply flow conduit 304, 103b and the return flow conduit 303, 102b. In the plug 100 shown in FIG. 3a, at the lower end of the plug-in region 101, there is a fixing 108 which is detachable by a detent and which on insertion snaps into the notches 306 correspondingly arranged on the socket region 301.

Figure 3B:
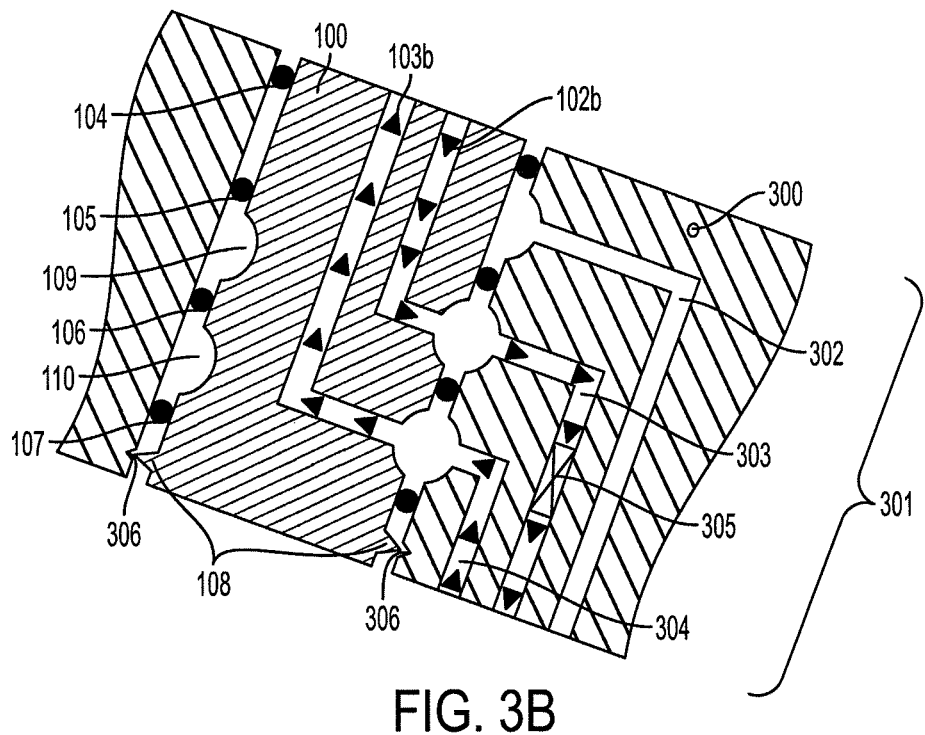
FIG. 3b illustrates a sectional view along the line A-B in FIG. 1 of a plug-in region plugged into a socket of a flexible cryoprobe.
Figure 4A:
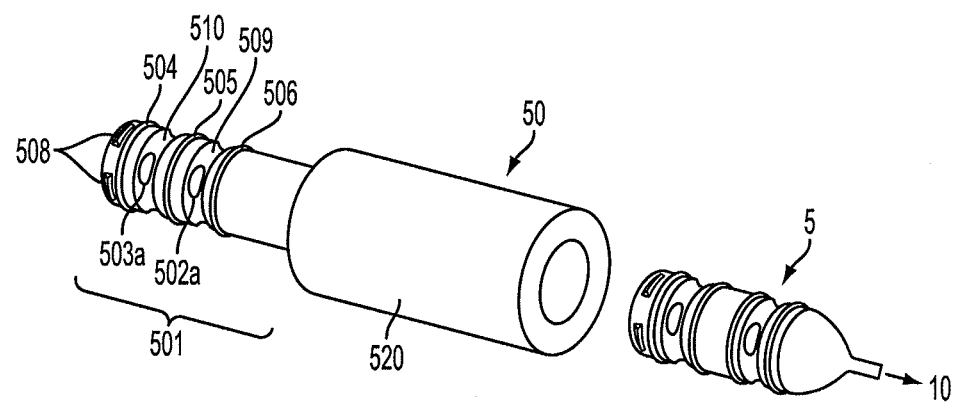
FIG. 4a illustrates a perspective view of an adapter for the plug-in region of a conventional rigid probe.
Figure 4B:
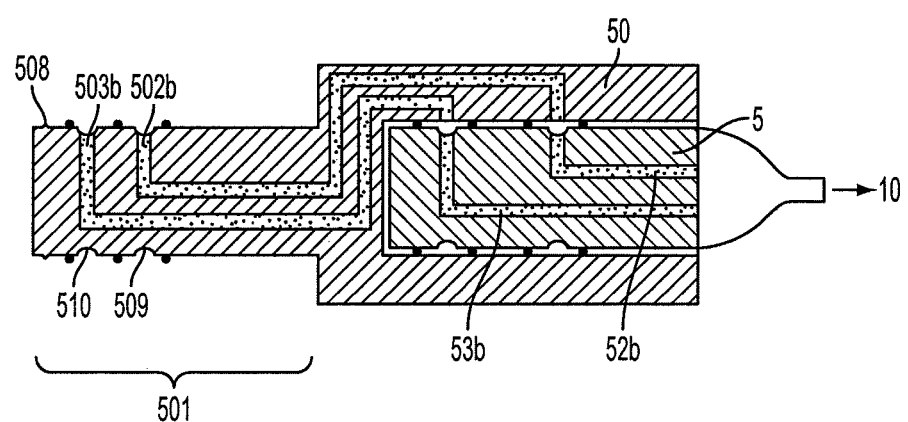
FIG. 4b illustrates a sectional view of an adapter for the plug-in region of a conventional rigid probe with an inserted plug.
Figure 5A:
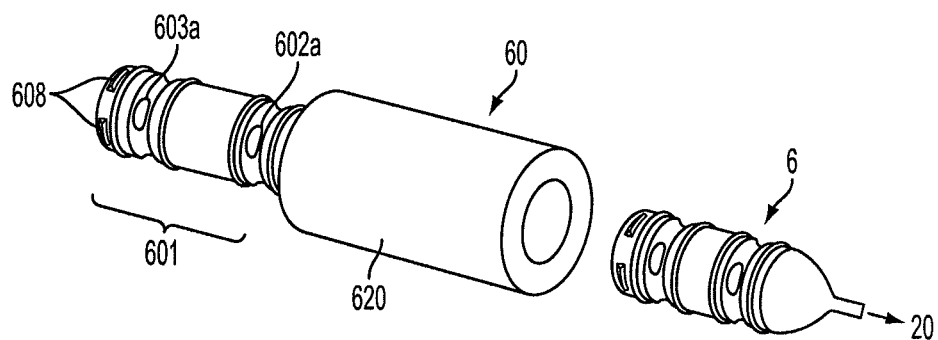
FIG. 5a illustrates a perspective view of an adapter for the plug-in region of a conventional flexible probe.
Figure 5B:
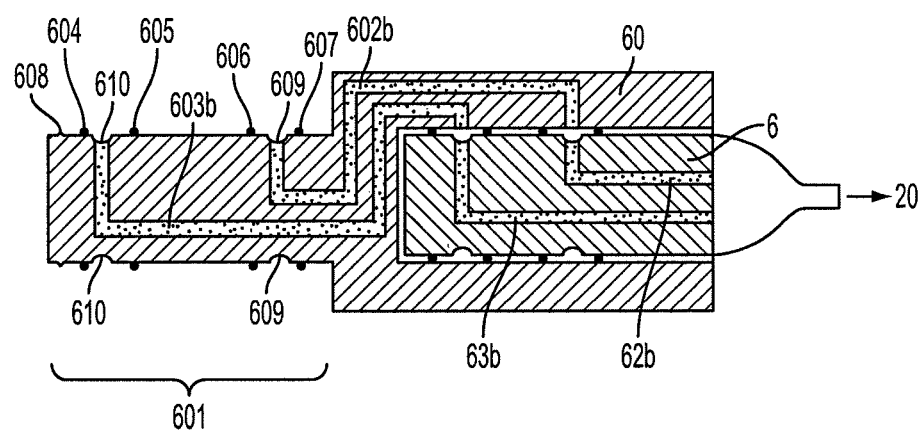
FIG. 5b illustrates a sectional view of an adapter for the plug-in region of a conventional flexible probe with an inserted plug.

There now follows a more detailed explanation of the structure of the present probe coupling and the interaction between the plug 100 and the socket 300 of the cryosurgical device with reference to the sectional drawing of the plug-in region 101 inserted in the socket region 301 in FIG. 3b.

In the control 30 of the cryosurgical device, a supply flow conduit 304 and the two return flow conduits 302, 303 lead to the socket region 301 of the socket 300, wherein, in the exemplary embodiment in FIG. 3b, the return flow conduit 303 of the socket 300 with a valve 305 is connected to the return flow conduit 102b of the rigid first cryoprobe 10 and the supply flow conduit 304 is connected to the supply flow conduit 103b of the rigid first cryoprobe 10. Due to this, on the discharge of the coolant gas through the valve 305 in the gas disposal device 41, the coolant gas is compressed below the inversion temperature and the rigid first cryoprobe thaws more quickly due to the reversal of the Joule-Thomson effect.

When the plug 100 of the rigid first cryoprobe 10 is inserted in the socket 300 of the cryosurgical device, the fixing 108 latches in the corresponding notches 306 of the socket 300 and hence ensures that the plug 100 is held reliably in the socket 300. When the plug 100 is inserted, the supply flow conduit 304 of the control 30 is automatically connected via the socket 304 to the supply flow conduit 103b of the rigid first cryoprobe 10 and the return flow conduit 303 of the control 30 leading to the gas disposal device 41 is automatically connected to the return flow conduit 102b of the rigid first cryoprobe 10, wherein the return flow conduit 303 of the control 30 leads through the valve 305 into the gas disposal device 41. The grooves 109, 110 surrounding the openings 102a, 103a ensure that the supply and return flow of the coolant gas is ensured in every possible position of the inserted plug 100.

The fixing of the plug 100, 200 in the socket 300 can also be implemented by other fixings suitable for the plugs 100, 200 of the cryoprobes 10, 20. The plug 100, 200 can, for example, also be attached by an external thread attached to the outside of the socket 300 and a nut attached movably to the upper plug-in region and corresponding to the external thread in the socket 300. In addition, the fixing of the plug 100, 200 in the socket 300 can also be achieved by a click seal or by a magnet attached at the lower end of the plug-in region 101 and/or a metal plate attached at the lower socket region 101. Furthermore, this should also include possible fixings for a plug 100 in a socket 300 known or evident to the person skilled in the art.

A further exemplary embodiment of a probe coupling is shown in FIGS. 4a, 4b, 5a, and 5b. This involves two adapters 50, 60 for the plugs of rigid and flexible cryoprobes in older models which are not suitable for use with the cryosurgical device. The adapter comprises a plug-in region 501, 601 suitable for use in the cryosurgical device and a socket 520, 620 compatible with the respective plug of the conventional models. Each plug-in region 501, 601 of the adapter 50, 60 comprises two openings 502a, 503a, 602a, 603a for the supply and return flow conduits 502b, 503b, 602b, 603b and comprises grooves 509, 510, 609, 610 surrounding the plug-in region at the respective height of the openings 502a, 503a, 602a, 603a. In addition, the openings 502a, 503a, 602a, 603a and the grooves 509, 510, 609, 610 are separated from each other in a gas-tight way by seals 504 to 506 and 604 to 607, in particular O-rings, in the inserted condition. At the lower end of the plug-in region 501, 601 of the adapter 50, 60, there is, for example, a detent 508, 608 suitable for fixing the adapter 50, 60 in the socket region 301 of the cryosurgical device. The openings 502a, 503a, 602a, 603a of the supply and return flow conduits 502b, 503b, 602b, 603b of the adapter 50, 60 are arranged so that on insertion in the socket 300 of the cryosurgical device of the present invention, they are each connected to the supply flow conduit 304 and return flow conduit 302, 303 suitable for the corresponding flexible or rigid cryoprobe 10, 20. In this regard, the supply flow conduit 53b of the conventional rigid cryoprobe 5 is connected via the supply flow conduit 503b of adapter 50 to the supply flow conduit 304 of the control of the cryosurgical device and the return flow conduit 52b of the conventional rigid cryoprobe 5 is connected via the return flow conduit 502b of adapter 50 to the return flow conduit 303 with a valve 305 of the control of the cryosurgical device. On insertion in the socket 300 of the cryosurgical device of the present invention, the supply flow conduit of a conventional flexible cryoprobe 6 is connected via the supply flow conduit 603b of adapter 60 to the supply flow conduit 304 and the return flow conduit of the conventional flexible cryoprobe 6 is connected via the return flow conduit 602b of adapter 60 to the return flow conduit 302 bypassing the valve 305.

Figure 6A:
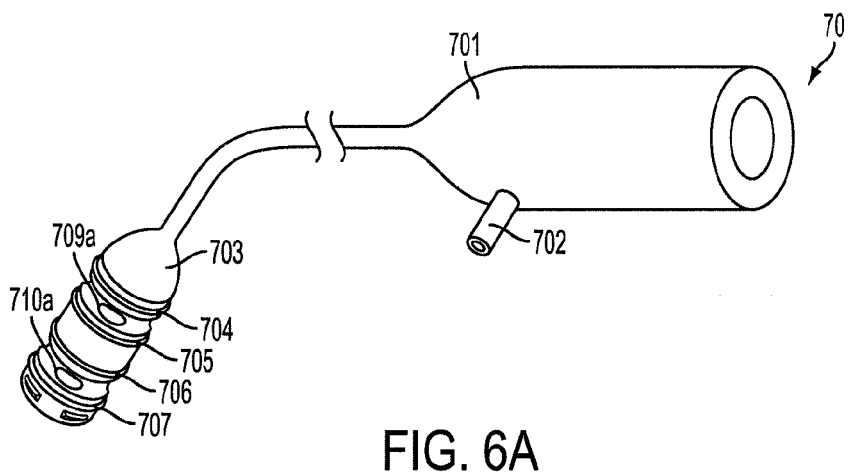
FIG. 6a illustrates a perspective view of an adapter for the socket region of a conventional cryosurgical device with a coupling for a return flow conduit surrounding the valve for the gas disposal.
Figure 6B:
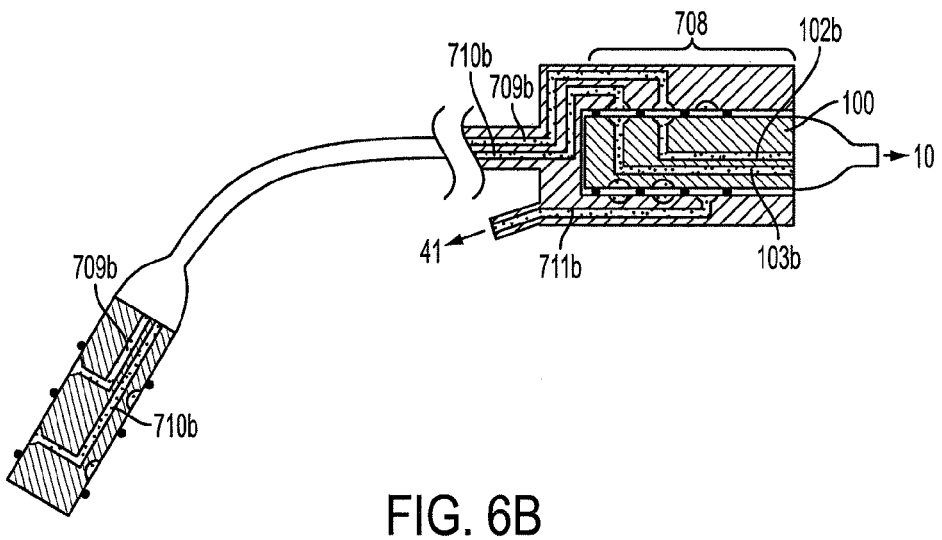
FIG. 6b illustrates a sectional view of an adapter for the socket region of a conventional cryosurgical device with an inserted rigid probe.
Figure 6C:
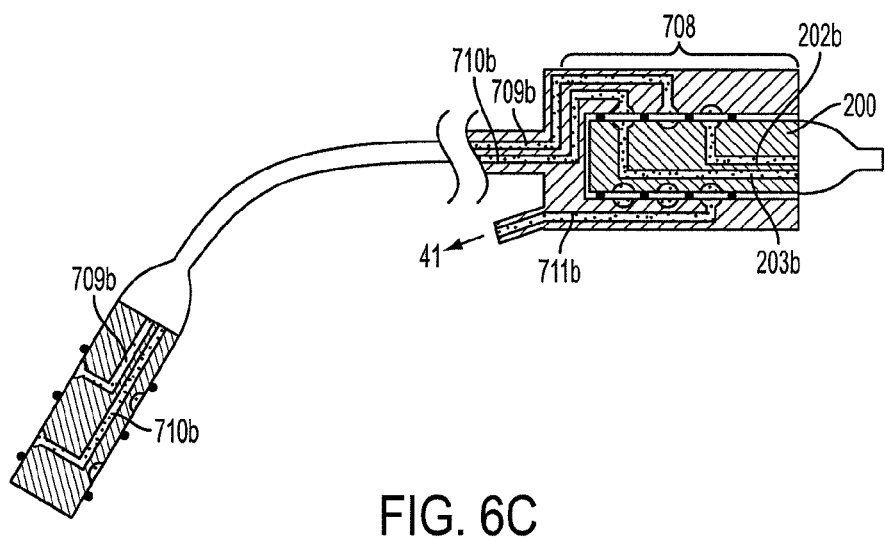
FIG. 6c illustrates a perspective view of an adapter for the socket region of a conventional cryosurgical device with an inserted flexible probe.

In another exemplary embodiment of a probe coupling, FIGS. 6a, 6b and 6c show an adapter 70 suitable for the attachment of the flexible and rigid cryoprobes 10, 20 of the invention for older models of a cryosurgical device. The adapter comprises a socket 701, a plug 703 attached thereto for attachment to a conventional cryosurgical device and a connecting pipe 702 protruding out of the lower outer part of the socket. An internal socket region 708 comprises three openings of conduits 709b, 710b, and 711b which are arranged so that on the insertion of flexible cryoprobe 20 of a cryosurgical device of the present invention, the supply flow conduit 203b of the flexible cryoprobe 20 is connected via the supply flow conduit 710b of the adapter 70 to the supply flow conduit of the conventional cryosurgical device and the return flow conduit 202b of the flexible cryoprobe 20 is connected via the return flow conduit 711b of the adapter 70 and via an external conduit (not shown in FIGS. 6a, 6b, 6c) without a valve to the gas disposal device of the conventional cryosurgical device and that, on the insertion of rigid cryoprobe 10 of a cryosurgical device of the present invention, the supply flow conduit 103b of the rigid cryoprobe 10 is connected via the supply flow conduit 710b of the adapter 70 to the supply flow conduit of the conventional cryosurgical device and the return flow conduit 102b of the rigid cryoprobe 10 is connected via the return flow conduit 709b of the adapter 70 to the return flow conduit of the cryosurgical device containing a valve. In addition, the openings 709a, 710a of the conduits 709b, 710b are separated from each other in a gas-tight way by seals 704, 705, 706, 707, in particular O-rings, in the inserted condition.

In a further exemplary embodiment, the adapters 50, 60, 70 can also be used for a connection between a conventional cryosurgical device and a conventional rigid or flexible cryoprobe. In this regard, the adapter 70 is inserted in the socket of the conventional cryosurgical device and the adapters 50, 60 placed on the respective plugs of the conventional flexible and/or rigid cryoprobes, which means the suitable connection between the supply flow- and return flow conduits of the flexible and/or rigid cryoprobe is ensured in each case.

The probe coupling can also be installed internally on a cryosurgical device comprising a device for controlling the ice-ball formation by means of correspondingly generated electro-magnetic fields or achieved by corresponding adapters on the cryosurgical device or on the plugs of the cryoprobes. Also possible are combinations of plugs with contacts to temperature sensors or electrical thawing aids.

At this point, reference is made to the fact that all the parts described above are claimed as inventive in their own right and in any combination, in particular the details shown in the drawings. The person skilled in the art is familiar with modifications.

The invention claimed is:

1. A cryosurgical device comprising:
   a first type of cryoprobe comprising a first-cryoprobe supply flow conduit and a first-cryoprobe return flow conduit;
   a second type of cryoprobe comprising a second-cryoprobe supply flow conduit and a second-cryoprobe return flow conduit;
   a socket comprising a socket supply flow conduit and two socket return flow conduits, wherein the first type of cryoprobe and the second type of cryoprobe are configured to be inserted into the socket such that only one of the first type of cryoprobe and the second type of cryoprobe is inside the socket at a time
   a control for a supply and a removal of a coolant gas to the first type of cryoprobe and the second type of cryoprobe when inserted into the socket;
   wherein the second-cryoprobe return flow conduit requires a different supply pressure or backflow pressure than the first-cryoprobe return flow conduit, and
   wherein the removal of the coolant gas from the second type of cryoprobe when inserted in the socket takes place via the second-cryoprobe return flow conduit and a first of the two socket return flow conduits and the removal of the coolant gas from the first type of cryoprobe when inserted in the socket takes place via the first-cryoprobe return flow conduit and a second of the two socket return flow conduits.

2. The cryosurgical device according to claim 1, wherein, when the first type of cryoprobe is inserted in the socket, the socket supply flow conduit and the second of the two socket return flow conduits are directly connected to a reservoir and a gas disposal device, respectively, and
   wherein, when the second type of cryoprobe is inserted in the socket, the socket supply flow conduit and the first of the two socket return flow conduits are directly connected to the reservoir and the gas disposal device, respectively.

3. The cryosurgical device according to claim 1, wherein a plug-in region of a plug portion of the first type of cryoprobe has a round cross section that can be inserted into an insertion region of the socket and comprises a first supply circumferential groove at an opening of the first-cryoprobe supply flow conduit and a first return circumferential groove at an opening of the first-cryoprobe return flow conduit, and
   wherein a plug-in region of a plug portion of the second type of cryoprobe has a round cross section that can be inserted into the insertion region of the socket and comprises a second supply circumferential groove at an opening of the second-cryoprobe supply flow conduit and a second return circumferential groove at an opening of the second-cryoprobe return flow conduit.

4. The cryosurgical device according to claim 3, wherein, when the first type of cryoprobe is inserted into the insertion region of the socket, spaces formed by the first supply circumferential groove and the first return circumferential groove of the plug-in region of the first type of cryoprobe are separated from each other by first gas-tight seals, and the openings of the first-cryoprobe return flow conduit and the first-cryoprobe supply flow conduit are respectively aligned to openings in the insertion region of the socket of the second of the two socket return flow conduits and the socket supply flow conduit, and
   wherein, when the second type of cryoprobe is inserted into the insertion region of the socket, spaces formed by the second supply circumferential groove and the second return circumferential groove of the plug-in region of the second type of cryoprobe are separated from each other by second gas-tight seals, and the openings of the second-cryoprobe return flow conduit and the second-cryoprobe supply flow conduit are respectively aligned to openings in the insertion region of the socket of the first of the two socket return flow conduits and the socket supply flow conduit.

5. The cryosurgical device according to claim 1, wherein an opening on an insertion region of the socket in fluid communication with the socket supply flow conduit is aligned with an opening of the first-cryoprobe supply flow conduit when a plug portion of the first type of cryoprobe is inserted into the insertion region of the socket and aligned with an opening of the second-cryoprobe supply flow conduit when a plug portion of the second type of cryoprobe is inserted into the insertion region of the socket.

6. The cryosurgical device according to claim 1, wherein one of the two socket return flow conduits has a valve for gas disposal and the second of the two socket return flow conduits does not have a valve for gas disposal,
wherein an opening on an insertion region of the socket in fluid communication with the socket return flow conduit having the valve for gas disposal is aligned with an opening of the first-cryoprobe return flow conduit when a plug portion of the first type of cryoprobe is inserted into the insertion region of the socket, and
wherein an opening on the insertion region of the socket corresponding to the return flow conduit not having the valve for gas disposal is aligned with an opening of the second-cryoprobe return flow conduit when a plug portion of the second type of cryoprobe is inserted into the insertion region of the socket.

7. The cryosurgical device according to claim 3, wherein, upon insertion of either the plug-in region of the plug portion of the first type of cryoprobe or the plug-in region of the plug portion of the second type of cryoprobe, the inserted plug-in region of the first type of cryoprobe or the second type of cryoprobe is fixably connected to the insertion region of the socket.

8. The cryosurgical device according to claim 7, wherein each of the plug-in region of the plug portion of the first type of cryoprobe and the plug-in region of the plug portion of the second type of cryoprobe is fixably connected to the insertion region of the socket by a fixing selected from the group consisting of a detachable click fixing, a fixing which is detachable by a detent, and a fixing formed by a magnet attached at a lower end of the respective plug-in region of the first or second type of cryoprobe and a metal plate or magnet attached to a lower socket region.

9. The cryosurgical device according to claim 1, wherein a plug-in region of a plug portion of the first type of cryoprobe is formed by a first separate adapter that is adapted to the first type of cryoprobe and a plug-in region of a plug portion of the second type of cryoprobe is formed by a second separate adapter that is adapted to the second type of cryoprobe.

10. The cryosurgical device according to claim 1, wherein an insertion region of the socket is formed by a separate adapter and the separate adapter is connected to at least one of the control of the cryosurgical device, a reservoir for coolant gas, and a reducing valve.

11. The cryosurgical device according to claim 4, wherein the first and second gas-tight seals are O-rings.

12. A cryosurgical device comprising:
a first type of cryoprobe comprising a first cryoprobe supply flow conduit, a first cryoprobe return flow conduit and a first cryoprobe plug;
a second type of cryoprobe comprising a second cryoprobe supply flow conduit, a second cryoprobe return flow conduit and a second cryoprobe plug;
a socket comprising a socket supply flow conduit and two socket return flow conduits, wherein the first type of cryoprobe and the second type of cryoprobe are configured to be inserted into the socket such that only one of the first type of cryoprobe and the second type of cryoprobe is inside the socket at a time
a control for a supply and a removal of a coolant gas to the first type of cryoprobe and the second type of cryoprobe when inserted into the socket;
wherein the second cryoprobe return flow conduit requires a different backflow pressure than the first cyroprobe return flow conduit, and
wherein the socket, the first cryoprobe plug and the second cryoprobe plug are adapted such that, when the second type of cryoprobe is inserted in the socket, the removal of the coolant gas from the second type of cryoprobe takes place via a first of the two socket return flow conduits and, when the first type of cryoprobe is inserted, the removal of the coolant gas from the first type of cryoprobe takes place via a second of the two socket return flow conduits.

* * * * *

UNITED STATES PATENT AND TRADEMARK OFFICE
CERTIFICATE OF CORRECTION

| | | |
|---|---|---|
| PATENT NO. | : 8,951,246 B2 | Page 1 of 1 |
| APPLICATION NO. | : 12/097491 | |
| DATED | : February 10, 2015 | |
| INVENTOR(S) | : Franz Geiselhart | |

It is certified that error appears in the above-identified patent and that said Letters Patent is hereby corrected as shown below:

In the claims,

In Column 10, line 20, in Claim 12, delete "wherein the first type of cryoprobe and the second type of cryoprobe are configured" and insert -- wherein the first cryoprobe plug and the second cryoprobe plug are configured --

Signed and Sealed this
Twelfth Day of April, 2016

Michelle K. Lee
*Director of the United States Patent and Trademark Office*